United States Patent
Toneby

[19]
[11] Patent Number: 6,083,520
[45] Date of Patent: Jul. 4, 2000

[54] BIOACTIVE FEED

[75] Inventor: Mark Toneby, Dalvägen, Sweden

[73] Assignee: Ewos Aktiebolag, Sweden

[21] Appl. No.: 09/020,687

[22] Filed: Feb. 9, 1998

Related U.S. Application Data

[63] Continuation of application No. 08/443,664, May 18, 1995, abandoned.

[30] Foreign Application Priority Data

May 19, 1994 [SE] Sweden .................................. 9401738

[51] Int. Cl.⁷ ...................................................... A01N 25/26
[52] U.S. Cl. .......................... 424/420; 438/498; 438/442; 438/184.1
[58] Field of Search ..................... 424/439, 474, 424/442, 484, 464, 438, 498, 420

[56] References Cited

U.S. PATENT DOCUMENTS

| | | |
|---|---|---|
| 5,093,128 | 3/1992 | Draguesku et al. . |
| 5,393,532 | 2/1995 | Wachtel et al. . |
| 5,401,515 | 3/1995 | Woodard et al. . |
| 5,411,746 | 5/1995 | Sigorino et al. . |
| 5,460,827 | 10/1995 | Sanderson et al. . |
| 5,472,710 | 12/1995 | Klokkers-Bethke et al. . |
| 5,472,714 | 12/1995 | Bourquin . |
| 5,541,170 | 7/1996 | Rhodes et al. . |

FOREIGN PATENT DOCUMENTS

| | | |
|---|---|---|
| 0 363 733 | 4/1990 | European Pat. Off. . |
| 0 682 874 | 11/1995 | European Pat. Off. . |
| 2 203 336 | 10/1988 | United Kingdom . |
| 2 249 466 | 5/1992 | United Kingdom . |
| 93/14645 | 8/1993 | WIPO . |
| 95/07028 | 3/1995 | WIPO . |

*Primary Examiner*—Thurman K. Page
*Assistant Examiner*—R. Bawa
*Attorney, Agent, or Firm*—Ratner & Prestia

[57] ABSTRACT

The present invention relates to a bioactive feed pellet comprising besides commonly used nutritionally valuable components, a biologically active ingredient such as a therapeutically or prophylactically active compound, a vaccine, a pigment, a vitamin, and/or an enzyme, whereby the bioactive ingredient has been applied to the pellet in the form of a primary coating dispersion and/or emulsion and/or solution in a fatty component or a mixture of dietary oil, said component or dietary oil comprising a triglyceride, and/or fatty acid thereof, having a melting point of above 35° C. in an amount of at least 0.05% by weight of the total weight of the pellet, and in an amount comprising at least 0.2% by weight of said coating, and that a further, second coating layer of an oily product has been applied after said coating dispersion, and/or emulsion and/or solution comprising the bioactive ingredient.

33 Claims, No Drawings

BIOACTIVE FEED

This is a continuation of U.S. application Ser. No. 08/443,664, filed on May 18, 1995 now abandoned.

DESCRIPTION

Technical Field

The present invention relates to a bioactive feed pellet comprising besides commonly used nutritionally valuable components, a biologically active ingredient such as a therapeutically or prophylactically active component, a vaccine, a pigment, a vitamin, a hormone, live microbial cells or an enzyme or other bioactive ingredient.

The object of the present invention is to obtain a feed pellet which comprises a bioactive ingredient and which can be stored under normal shelf conditions.

Another object is to obtain such a pellet providing for a safe and accurate administration of a bioactive ingredient.

A further object is to provide a pellet in such a form that air contamination by active components during manufacture and handling are avoided.

A yet further object of the present invention is to provide palatability to pellets containing an added non-palatable component.

Background of the Invention

The administration of bioactive ingredients, in particular therapeutically and prophylactically active compounds, oral vaccines, enzymes, vitamins, to animals is often requested, but is also as a rule subject to many problems. The most simple way of administering bioactive compounds to an animal is to use the feed as a carrier for oral route of administration. This can be done as most animals obtain feed or feed supplements in the form of feed pellets, to which a metered quantity of the bioactive ingredient or compound can be added, in order to be able to administer a certain dosage per day or event of administration.

However, feed pellets are most often produced by methods involving heating of the ingredients. Pelletizing or extrusion involve subjecting the product to heat. When it comes to the common nutrients this is a negligible problem, as long as only minor parts are inactivated, but when regarding bioactive ingredients which are to be administered in certain, predetermined amounts, one requires a guaranteed concentration in the pellets, and can thus only accept negligible loss of the amounts of bioactive ingredients added. Often bioactive compounds, such as pharmaceuticals, vitamins, and enzymes and the like are more sensitive to heat decomposition than are the nutrients.

Some bioactive ingredients are sensitive to hydrolysis or oxidation as well, and thus need protection from the atmosphere of the environment, either during manufacture or during storage.

On the market today are sold feed pellets for fish comprising drugs applied in a coating of common fish oil included in the feed mass or dry coated on the finished fish feed pellets, all methods being non-optimal with regard to the inclusion of bioactive components in the feed.

Thus, there are a number of technical problems to be solved to be able to administer bioactive compounds via a feed pellet without deteriorating the component or reducing the accuracy of dosing.

Description of the Present Invention

It has now surprisingly been shown possible to solve the present problems and to meet the requirements set by means of the present invention which is characterized in that the bioactive ingredient has been applied to the pellet in the form of a primary coating dispersion, and/or emulsion and/or solution in a fatty component or a mixture of dietary oil, said component or dietary oil comprising a triglyceride, and/or fatty acid thereof, having a melting point of above 35° C. in an amount of at least 0.05% by weight of the total weight of the pellet, and in an amount comprising at least 0.2% by weight of said coating, and that a further, second coating layer of an oily product has been applied onto said coating dispersion and/or emulsion and/or solution comprising the bioactive ingredient.

Further characteristics are evident from the accompanying claims.

The terms "bioactive ingredient", "bioactive compound", "drug", "vitamin", "vaccine", "enzyme", "pigment" and others relating thereto, have been used in the singular hereinabove. However, it shall be understood that such compounds can be used two or more together, such as a number of vitamins, or in mixtures from differently active groups, such as a drug and vitamins together, if not otherwise indicated.

The primary coating comprises an oil, and a suspending aid and the bioactive compound. The suspending aid provides for dispersion and/or emulsion and/or solution properties of the bioactive compound. The suspending aid consists of a triglyceride and/or a fatty acid thereof having a melting point above 35° C., i.e. being solid at temperatures below 35° C.

The triglycerides and the fatty acids thereof are selected from the group consisting of those substantially solid at temperatures below 35° C. including hydrogenated rape seed oil, hydrogenated soya bean oil, hydrogenated sunflower seed oil, hydrogenated olive oil, hydrogenated palmoil, hydrogenated coconut oil, tristearin, palmitic acid, hydrogenated fish oil, stearic acid and animal fats, whereby those being saturated are preferred.

The amount of triglyceride and/or fatty acid thereof added to the bulk dietary oil, such as fish oil, as a suspending aid for the bioactive compound is at least 0.2% by weight of the fish oil and may amount to as much as 10% by weight, whereby 0.5 to 4% by weight is a preferred range.

In case the bioactive compound to be added is not miscible with the suspending aid, a dispersing or emulsifying agent can be added to improve mixing properties still further. Such emulsifiers are saturated distilled monoglycerides, polyunsaturated polyglycerol esters of fatty acids, sorbitan fatty acid esters, and others known to the one skilled in the art colloidal particulate emulsifiers. Saturated monoglycerides are preferred.

The primary coating provides for an even distribution of the bioactive compound, and provides for an attachment of the bioactive compound to the pellet as well. The coating dispersion and/or solution further provides for a transport of the bioactive compound into the pellet, either in solid particle form or in liquid emulsion form or in dissolved form. The active component is present in the dietary oil in an amount of 1 to 25%, but can be as low as 1 ppm, and as high as 35%.

Using the present dispersion, and/or emulsion and/or solution technique, protection against hydrolysis, protection against oxidation, stabilization, a better uptake and a homogenous distribution is obtained. Further, dusting problems are avoided during manufacture and handling thereby avoiding an environmental problem and reducing health hazards.

The second coating can consist of an untreated oil, oil provided with the suspension aid or oil built up as the primary coating oil but containing another bioactive component.

As transport and shipping of the bioactive compound takes place there is a reduced risk for scratching off of the coating by abrasion during transport and storage between the pellets, and thereby there is a smaller risk of reduced amounts of bioactive compound being present on/in the pellets at the moment of administration as well as a reduced risk for environmental problems when handling pellets and empty product bags or containers.

Drugs to be administered are of different types, and thus antibiotics (penicillins, tetracyclins etc), anti-inflammatory agents, biologicals and others are contemplated.

Prophylactic treatment compounds such as vaccines, are also an important group of bioactive compounds to be administered to animals to improve health status. This group also includes microorganisms e.g. of the lactobacilli type, which may provide an adequate gastro-intestinal flora of microorganisms.

Digestion active enzymes are another important group of bioactive compounds to be administered to animals, as well as vitamins and hormones to improve health and growth in general as well as palatability enhancers.

Another group of bioactive components to be used is poisons, such as rat poison, or insecticidal systemically acting components fed to animals.

In the farming of salmon and other fishes, but in particular salmonids, one important factor has become to administer pigments to mimic natural pigment uptake and to improve flesh colour. The losses during production such as extrusion can, however, be extremely high and may amount to 40%. The costs of the pigments are high as well, and every percentage of pigment saved reduces costs. Pigments are further susceptible to oxidation during storage and further losses can be encountered in that stage as well. Pigments normally used today are astaxanthin and canthaxanthin. A further factor to consider is their poor uptake and retention by the fish.

The present invention will now be described in more detail in the following by reference to some non-limiting examples. It will be understood that the examples are given as exemplification, and shall not be regarded as limiting the scope set forward in the accompanying claims.

The invention will be described in connection with a fish feed pellet, in connection with which the present invention has been developed, and where the largest technical problems are encountered and are solved by application of the present invention.

The basic fish feed pellets used in the examples below, are intermediates for feed products on the market named Vextra C, 9 mm, and Vextra Gold, 9 mm, respectively, both sold by Ewos Aqua A/S, Norway, whereby the pellets as used have not been provided with their final fat content, but are as indicated an intermediate product.

The pellets were taken warm directly from the production line, sieved to be freed from dust under warm conditions. The fish feed pellets contain protein, carbohydrates and fat, whereby the fat content amounts to about 8–10% by weight, basically due to the content of fish meal containing endogenous fat. Then the hydrophobic coating was applied in heated conditions, 45° C., and 65° C., respectively. Total batch size in each run was 25 kg (normally 21.25 kg of pellets, and 3.75 kg of coating) The first coating was applied over 30 sec. and the second coating was applied over 60 sec using a Forberg mixer. In some tests the pellets were abraded using a Pellet Abrasion Tester apparatus in order to determine dusting, reduction of activity, penetration of the bioactive component into pellet and other conditions.

EXAMPLE 1–4

21.25 kg of pellets (Vextra i/C, 9 mm) were coated with a hydrophobic coating consisting of fish oil (7.9–7.6% by weight of pellets) and hardened (hydrogenated) vegetable oil (rape seed oil) (0–0.3% by weight of the pellets), and 70 mg astaxanthin, and 120 mg canthaxanthin at 45° C. and 65° C., respectively in accordance with Table 1 below. The pellets were then coated with a second coating consisting of fish oil (6.7–7.0% by weight of the pellets, and 0.3–0% by weight of the pellets of hardened vegetable oil (rape seed oil)) in accordance with Table 1 below. The pellets obtained were tested for their contents of astaxanthin after 6, and 3 months, respectively, whereby the tests have been run on different batches, as evident from Tables 2 and 3, respectively. The pellets were run in a Pellet Abrasion Tester apparatus to determine abrasion after 500 revolutions at 50 rpm followed by determination of the remaining quantity of astaxanthin in the pellets.

TABLE 1

| Example | Coating 1 | | Coating 2 | |
| --- | --- | --- | --- | --- |
|  | Fish oil (%) | Hardened oil (%) | Fish oil (%) | Hardened oil (%) |
| 1 (45° C.) | 7.9 | 0 | 7.0 | 0 |
| 2 (45° C.) | 7.6 | 0.3 | 7.0 | 0 |
| 3 (65° C.) | 7.6 | 0.3 | 7.0 | 0 |
| 4 (65° C.) | 7.9 | 0 | 6.7 | 0.3 |

TABLE 2

| Example | Storage | | |
| --- | --- | --- | --- |
|  | 0 | 6 | 6A* months |
| 1 | 51.5 (74) | 55.8 (80) | 41.0 (59) |
| 2 | 64.5 (93) | 63.8 (91) | 62.8 (90) |
| 3 | 64.5 (92) | 67.9 (97) | 66.7 (95) |
| 4 | 65.8 (94) | 63.8 (91) | 65.9 (94) |

TABLE 3

| Example | Storage | | |
| --- | --- | --- | --- |
|  | 0 | 3 | 3A* months |
| 1 | 59.8 (85) | 61.1 (87) | 59.5 (85) |
| 2 | 67.2 (96) | 62.7 (90) | 64.2 (92) |
| 3 | 66.0 (94) | 66.1 (94) | 66.2 (95) |
| 4 | 74.1 (106) | 75.9 (108) | 74.5 (106) |

*A stands for abraded pellets.

As evident from above, the present coating method (Ex. 2–4) provides for a much more stable and accurate astaxanthin content than a method according to prior art, viz. when not using a suspending aid (saturated triglyceride or fatty acid thereof), but having the astaxanthin suspended in the fish oil as such.

EXAMPLE 5

To a mixture of 336.9 kg of warm fish oil (capelin) and 7.0 kg of hydrogenated rape seed oil 57.1 kg of oxolinic acid were added under vigorous stirring. The oil/drug mixture was added to 4000 kg of uncoated fish feed pellets (Vextra intermediate, 9 mm) in a Forberg mixer. In a second step 475 kg of warm fish oil (capelin) were coated onto the pellets in the Forberg mixer. The total quantities of finished pellets were divided into 19 production batches containing 250 kg each. Mean analytical concentration of oxolinic acid in all batches was 10.48±0.17 g/kg (S.D.). It was also found that more than 50% of the oxolinic acid quantity had penetrated into an inner core comprising 78% of the pellet.

EXAMPLE 6

To a warm mixture of oil of 144.7 g of fish oil (capelin), 4.5 g of hydrogenated rape seed oil and 0.8 g of ethoxylated castor oil 10 g of oxolinic acid were added while stirring. The mixture was homogenized and added to 1680 g of uncoated fish feed pellets (Vextra Gold, intermediate pellet, 6 mm). This pellet was coated in a second step with 160 g of pure fish oil (capelin).

The invention as been exemplified above with regard to bioactive fish feed pellets, but the invention can be applied to other types of feed pellets as well, including pellets for mono-and polygastric animals, such as pigs, horses, calves, young sheep, cows, sheep, goats, fowl and poultry, such as chickens, turkeys, and ducks, deer, reindeer, cats and dogs, whereby the dietary fat used should be any palatable to the type of animal intended to be fed. Another group of animals comprises laboratory animals, whereby different test compounds can be incorporated, and zoo animals.

What is claimed is:

1. A bioactive feed pellet comprising:
   a basic feed pellet containing protein, carbohydrates and fat; and
   a biologically active ingredient selected from the group consisting of a therapeutically active component, a prophylactically active component, a vaccine, a pigment, a vitamin and an enzyme, wherein said basic feed pellet is coated with a primary coating, said primary coating containing said biologically active ingredient and being selected from the group consisting of a solution of said biologically active ingredient in a dietary oil mixture, a dispersion of said biologically active ingredient in a dietary oil mixture and an emulsion of said biologically active ingredient in a dietary oil mixture, said dietary oil mixture comprising a dietary oil and a suspending aid, said suspending aid having a melting point of above 35° C. and being selected from the group consisting of a triglyceride and a fatty acid thereof, said suspending aid being present in an amount of at least 0.05% by weight of said basic feed pellet and in an amount of at least 0.2% by weight of said primary coating, said primary coating containing from 1 ppm to 35% by weight of said biologically active ingredient with respect to said dietary oil of said primary coating, and wherein said basic feed pellet is coated with a secondary coating selected from the group consisting of an untreated oil, oil provided with said suspending aid, and oil built up as the primary coating oil and containing another bioactive component.

2. The bioactive feed pellet according to claim 1, wherein said suspending aid is selected from the group consisting of saturated triglycerides and fatty acids thereof of the group consisting of hydrogenated rape seed oil, hydrogenated soya bean oil, hydrogenated sun flower seed oil, hydrogenated olive oil, hydrogenated palm oil, hydrogenated coconut oil, tristearin, palmitic acid, hydrogenated fish oil, stearic acid, and animal fat.

3. The bioactive feed pellet according to claim 2, wherein said suspending aid is present in an amount of at least 0.2% by weight of the dietary oil.

4. The bioactive feed pellet according to claim 3, wherein said suspending aid is present in an amount of up to 10% by weight of the dietary oil.

5. The bioactive feed pellet according to claim 4, wherein said suspending aid is present in an amount of 0.5 to 4% by weight of the dietary oil.

6. The bioactive feed pellet according to claim 5, wherein said primary coating further contains an additive selected from the group consisting of a dispersing agent, an emulsifying agent and a mixture thereof.

7. The bioactive feed pellet according to claim 6, wherein said biologically active ingredient is selected from the group consisting of a therapeutically active compound and a prophylactically active compound.

8. The bioactive feed pellet according to claim 6, wherein said biologically active ingredient is a vaccine.

9. The bioactive feed pellet according to claim 6, wherein said biologically active ingredient is a vitamin.

10. The bioactive feed pellet according to claim 6, wherein said biologically active ingredient is an enzyme.

11. The bioactive feed pellet according to claim 6, wherein said biologically active ingredient is a pigment.

12. The bioactive feed according to claim 11, wherein said secondary coating contains a biologically active ingredient.

13. The bioactive feed pellet according to claim 1, which is a fish feed pellet to be administered to fish in fish farming.

14. The bioactive feed pellet according to claim 1, which is a poultry or fowl feed pellet.

15. The bioactive feed pellet according to claim 1, which is a feed pellet for ruminants.

16. The bioactive feed pellet according to claim 1, which is a bovine feed pellet.

17. The bioactive feed pellet according to claim 1, which is a cat feed pellet.

18. The bioactive feed pellet according to claim 1, which is a dog feed pellet.

19. The bioactive feed pellet according to claim 1, which is a horse feed pellet.

20. The bioactive feed pellet according to claim 1, which is a laboratory animal feed pellet.

21. The bioactive feed pellet according to claim 1, which is a zoo animal feed pellet.

22. The bioactive feed pellet according to claim 1, wherein the bioactive component is a poisonous component.

23. The bioactive feed pellet according to claim 1, wherein the biologically active ingredient is selected from the group consisting of rat poison and systemic insecticides.

24. The bioactive feed pellet according to claim 1, wherein said suspending aid is present in an amount of at least 0.2% by weight of the dietary oil.

25. The bioactive feed pellet according to claim 1, wherein said suspending aid is present in an amount of up to 10% by weight of the dietary oil.

26. The bioactive feed pellet according to claim 1, wherein said suspending aid is present in an amount of 0.5 to 4% by weight of the dietary oil.

27. The bioactive feed pellet according to claim 1, wherein said primary coating further contains an additive selected from the group consisting of a dispersing agent, all emulsifying agent and a mixture thereof.

28. The bioactive feed pellet according to claim 1, wherein said biologically active ingredient is selected from the group consisting of a therapeutically active compound and a prophylatically active compound.

29. The bioactive feed pellet according to claim 1, wherein said biologically active ingredient is a vaccine.

30. The bioactive feed pellet according to claim 1, wherein said biologically active ingredient is a vitamin.

31. The bioactive feed pellet according to claim 1, wherein said biologically active ingredient is an enzyme.

32. The bioactive feed pellet according to claim 1, wherein said biologically active ingredient is a pigment.

33. The bioactive feed pellet according to claim 1, wherein said biologically active ingredient has a delayed release activity.

* * * * *